United States Patent [19]

Makoui et al.

[11] Patent Number: 4,911,700

[45] Date of Patent: Mar. 27, 1990

[54] CROSS-LINKED MICROFIBRILLATED CELLULOSE PREPARED FROM PURE GENERATING PARTICLES

[75] Inventors: Kambiz B. Makoui, Menasha, Wis.; Pronoy K. Chatterjee, Spotswood, N.J.

[73] Assignee: McNeil-PPC, Inc., Milltown, N.J.

[21] Appl. No.: 943,100

[22] Filed: Dec. 18, 1986

Related U.S. Application Data

[62] Division of Ser. No. 757,568, Jul. 22, 1985, Pat. No. 4,767,848.

[51] Int. Cl.$^4$ .................. A61F 13/16; A61F 13/18; D21H 3/00; D06M 13/12
[52] U.S. Cl. ..................... 604/376; 604/904; 604/365; 604/375; 8/116.1; 8/116.4; 8/182; 162/157.6; 162/182
[58] Field of Search ............. 604/365, 367, 369, 374, 604/375, 376, 383, 384, 377, 904; 106/122; 162/146; 8/116.1, 116.4, 185, 186; 536/56

[56] References Cited

U.S. PATENT DOCUMENTS

| | | | |
|---|---|---|---|
| 2,117,392 | 5/1938 | Banigan | 106/122 |
| 3,241,553 | 3/1966 | Steiger | 128/156 |
| 3,891,577 | 6/1975 | Kershaw et al. | 106/122 |
| 3,932,209 | 1/1976 | Chatterjee | 162/146 |

Primary Examiner—Paul Lieberman
Assistant Examiner—John F. McNally
Attorney, Agent, or Firm—Andrea L. Colby

[57] ABSTRACT

Adsorbent retentive pulp is described which is capable of retaining good adsorbency even after having been highly compressed. The pulp is produced by subjecting a microfibrillated pulp slurry to pore generation with pore generating particles and to cross-linking with a cross-linking agent.

17 Claims, No Drawings

CROSS-LINKED MICROFIBRILLATED CELLULOSE PREPARED FROM PURE GENERATING PARTICLES

This is a division of application Ser. No. 757,568, filed July 22, 1985, now U.S. Pat. No. 4,767,848.

BACKGROUND OF THE INVENTION

This invention relates to absorbent, retentive cellulose pulp which is capable of retaining good absorbency even after having been highly compressed. This pulp is provided for use in absorbent products such as sanitary napkins, catamenial tampons, diapers, dressings or the like which are used for absorbing body fluids.

For many years, cellulose pulp has been utilized for absorbing body fluids. Wood pulp has been found most suitable for such products primarily because it is an inexpensive, readily available absorbent material. Such wood pulp is generally derived from soft wood trees such as southern pine and the like and is commercially treated in chemical pulping processes such as the kraft or sulfite processes during which the trunks and branches of trees are reduced to wood pulp fibers and non-fibrous substances such as gums, resins and lignin are chemically removed. The resulting wood pulp is sometimes bleached and then formed into board for subsequent disassociation into pulp fluff to be used in the aforementioned products.

Although pulp fluff derived from the conventional process steps has, in the past, been successfully employed in body fluid absorption products, the art has increasingly sought to improve the absorption capacity and fluid retention properties of wood pulp. Many suggestions have already been advanced, generally directed towards chemical modifications of the cellulose polymer of which the wood pulp fibers are composed. While these efforts have met with some success, the resulting products are substantially more expensive than native wood pulp and suffer from some peculiar drawbacks such as brittleness or slow wicking rates.

It has long been known that the absorbency of cellulosic fibers may be improved by wet cross-linking the fibers. Thus, U.S. Pat. No. 3,241,553 discloses such cross-linking in order to provide absorbent fibrous products which have improved absorbency as well as the ability to retain greater amounts of absorbed fluids when subjected to pressures which tend to squeeze out the fluids absorbed. There is, however, no disclosure in said U.S. Pat. No. 3,241,553 concerning the cross-linking of microfibrillated fibers.

The need for a relatively inexpensive, simple process for treating native cellulose fibers to increase their absorption capacity and fluid retention properties has been met to a limited degree by the process disclosed by Chatterjee, et al. in U.S. Pat. No. 4,474,949. Chatterjee, et al. disclosed a process of mechanically beating a dispersion of cellulose fibers to a degree such that at least the outermost of the secondary walls of the cellulose fibers were essentially completely disintegrated to microfibrillar form followed by the freeze drying of the beaten dispersion. The resultant material possesses excellent absorption properties at low densities, but poor absorption properties at higher densities. In addition, the mechanical strength of this material is too low since it collapses in contact with water under a confining pressure.

Furthermore, the freeze drying step of Chatterjee, et al., requires a lengthy production time of about 90 hours. Accordingly, there is a need for a much faster relatively inexpensive, simple process for treating native cellulose fibers to increase their absorption capacity and fluid retention properties, not only at low densities but also at higher densities.

It is an object of the present invention to provide a thin densified and flexible material to be utilized as an insert or entirely as an ultra-thin sanitary product. This material possesses high absorption and retention properties coupled with a fast wicking rate to absorb body fluid. The material should also demonstrate a Z direction swelling in the wet state and have a high structural integrity so that it can be easily handled. The final abosrption properties of the product can be varied to some extent by varying the size and amount of pore generating particles used in the process of the present invention. The expression "Z direction" as used herein is intended to signify the direction of initial compression of the compressed product.

SUMMARY OF THE INVENTION

In accordance with the object and principles of the present invention, a highly absorbent, retentive cellulose fiber may be produced in a relatively short period of time, which fiber retains good absorbency and retention even after having been highly compressed.

The absorbent retentive pulp of the present invention is produced by first providing a slurry of cellulose fibers in a first liquid medium consisting of water or a non-aqueous solvent, the fibers having been extensively beaten to a degree such that at least the outermost of the secondary walls of the cellulose fibers are essentially completely disintegrated into microfibrillar form. Thereafter, dispersible pore generating particles which are insoluble in the first liquid medium are added to the slurry, and subsequently the port generating particles are dispersed. The term "dispersed" is used herein to signify that the particles may be removed with a solvent, or in the instance wherein the particles are heat decomposable they may be removed by means of heat. A cross-linking agent is added to the slurry either before, during or after the addition of the pore generating particles. The first liquid medium is then evaporated and the resulting solid moist cake is heat cured. The expression "heat curing" as used herein is intended to signify cross-linking by application of heat. Thereafter, the heat cured cake is washed with a second liquid medium in which the pore generating particles are soluble, to remove the pore generating particles and other impurities. The resulting cake is then dried. In the instance wherein the pore generating particles are heat decomposable, they may be removed by heating. Further, in the instance wherein the cross-linking agent is added after the heat decomposable pore generating particles have been removed, the cake is reslurried in the first liquid medium, the cross-linking agent is added, the first liquid medium is again evaporated and the resulting solid moist cake is heat cured and dried. Preferably, the resultant pulp is pressed in order to produce a densified thin sheet.

The microscopic structure of the cellulose pulp derived from the teachings of this invention is similar to that disclosed in U.S. Pat. No. 4,474,949 which is incorporated herein by reference. Thus, if the pulp of the present invention were to be observed under a microscope, the fibrils released from the starting cellulose fibers by the beating step would appear, after the dispersion is cross-linked and treated with the pore generating particles, but before the final densification step, to be in the form of discrete platelets or sheets comprising freed fibrils in compressed form. The sheets tend to appear as discontinuous walls surrounding and defining cellular voids. Although the microscopic structure of the product of the present invention is similar to that of the product of U.S. Pat. No. 4,474,949, nevertheless the cross-linking step of the present process provides a pulp which has a surprisingly increased absorption capacity and fluid retention even after having been highly compressed, the cross-linking having formed intermolecular cross-links between macromolecular chains. Such compressed sheet also highly resilient (demonstrating a Z direction swelling) in the wet state.

DETAILED DESCRIPTION OF THE INVENTION

In accordance with the invention, there is provided a dilute dispersion (preferably in aqueous medium) of fibrous cellulose which has been beaten to an extensive degree to free microfibrils from the fibrous structure. Although water is the preferred medium in which this initial beating take place, other suitable non-aqueous media may also be utilized for this purpose.

While the preferred form of the starting cellulose fibers is chemical wood pulp derived from such pulping processes as kraft or sulfite pulping, it will be understood that almost any source of cellulose fibers is suitably employed. Accordingly, in addition to wood pulp, such diverse sources of cellulose fibers may include hemp, baggase, cotton and the like.

Irrespective of the plant source, cellulose fibers comprise cellulose chains, consisting of cellobiose units, laid down in a parallel arrangement with the long chained molecules strongly associated through secondary forces e.g. hydrogen bonds. This association of the cellulose chains results in a very uniform crystalline structure known as micelles of microcrystallites. The micelles are associated in the plant into long thread-like structures known as microfibrils. The association of the micelles into microfibrils is such that spaces or dislocations exist between micelles; such spaces, being of the order of about 15–20 angstrom units (A°), allowing liquid to migrate into the microfibril and accounting for at least part of the absorbency and retention properties of the cellulose fiber. High magnification photographs show that microfibrils of wood cellulose are filaments about 35 A° in breadth with a periodic variation in electron density along their lengths. Based on this observation, it has been proposed that the wood pulp microfibril is in the shape of a flat ribbon wound in the form of a tight helix.

The cellulose fiber itself is composed of layers of associated microfibrils. The outer layer is termed the primary wall and the inner layers are termed secondary walls which are further classified as $S_1$, $S_2$ layers, etc.

As described above, it is known, in the art of making paper, to beat or mechanically work a fiber slurry to free some microfibrils on the very outer layer of the cellulose fiber. The purpose of this beating treatment in the paper art is to enhance bonding. Great care, heretofore, has been taken to avoid damaging the inner layers.

In accordance with the teachings of U.S. Pat. No. 4,474,949, such a beating step is carried further to the point where at least the outermost of the secondary walls is essentially completely disintegrated to microfibrillar form. Preferably, the starting cellulose fibers are first dispersed in a dilute aqueous slurry. Such a slurry should have a solid content ranging from about 0.5 to about 10.0% and still more preferably, from about 1.5 to about 6.0 %.

The slurry is next passed to a beating station where it is mechanically worked to free microfibrils to a suitable degree. The method and apparatus for beating the slurry are not critical provided that a sufficient degree of microfibrillation is accomplished. Accordingly, commercially available equipment such as the Hollander, Jordan, or disk refiner type of beaters may be employed. The Hollander beater is an apparatus wherein the slurry is introduced into a tub and forced to pass under the nip formed between a corregated roller and a plate. As the roller is turned, a shearing force is exerted on the fibers in the nip. The Jordan type of beater employs two nesting cones with an annular space in between. The inner cone reciprocates so that the slurry, introduced into the annular space, is sheared. In the disk refiner, two round plates are in a face to face relationship and at least one of the plates is provided with ribs and at least one of the plates rotates. The slurry is introduced between the faces of the plates and is sheared by the rotating action. There exists still other suggestions for producing microfibrillar pulp and these are equally useful in carrying out this invention. One such suggestion is found in U.S. Pat. No. 4,374,702 issued on Feb. 22, 1983 to Turbak, et al.

It has been found that sufficient beating has occurred when the resulting fibers have been reduced to a Canadian Standard Freeness value of less than 100 and preferably less than 50. The period of time during which a slurry of a particular dilution, with a particular type of fiber is beaten in a particular beating apparatus is easily correlated to the Canadian Standard Freeness value of the finished product by a series of simple experiments. It will be understood that because the parameters which effect beating time may vary greatly and still produce a beaten slurry usable in accordance with the teachings of this invention, no generalization can be made with respect to such beating time.

In said U.S. Pat. No. 4,474,949, when using a Valley Beater, Model No. 73-13-1-1/2 Niagra, obtained from the Voith Company of Appleton, Wis. and beating a slurry of loblolly pine bleached kraft pulp having a solid content of 2%, suitable beating times ranged from 120 to about 160 minutes. The microfibrillated pulp, utilized in accordance with the present invention may also be prepared by soaking a southern pine bleached kraft pulp board with water and beating it on a Valley Beater at a consistency of 2%.

After the dilute slurry of microfibrillated fibers is provided, pore generating particles are added and, in addition, a cross-linking agent is added to the slurry either before during or after the addition of the pore generating particles. The pore generating particles may have a particle size range of between 0.1 and 5.0 (and preferably between 0.1 and 1.0) mm equivalent spherical diameter. The pore generating particles eliminate the need for a freeze-drying operation such as that shown in U.S. Pat. No. 4,474,949. In the latter patent, during the freezing step, the growth of ice crystals compresses the microfibrils together in the ice crystal grain boundaries and form a sheet-like structure. Subsequent sublimation of the ice crystals produce a material with tremendous void volume. It has now been found, in accordance with the present invention, that when pore generating particles are used to replace the function of ice crystals in preventing fiber collapse, micrographs of the pore structure of the pulp of the present invention are very similar to those illustrating the pulp produced by the freeze-drying process of U.S. Pat. No. 4,474,949. It is to be noted that a large number of pore generating particles may suitably be used in accordance with the present invention. To be useful, in accordance with this invention, the pore generating particles need only be insoluble in a first liquid medium in which the microfibrillated pulp is suspended, but must be readily soluble in a second liquid medium which is utilized to wash out the pore generating particles after the pulp, treated with a cross-linking agent, is subsequently cured. Thus, in the instance wherein the pore generating particle consists of a water soluble substance such as sodium sulfate or sodium chloride, the microfibrillated pulp is initially suspended in acetone, in which the sodium sulfate or sodium chloride is insoluble, and, ultimately, the sodium sulfate or sodium chloride particles are washed out of the cured cakes with water in which the particles are soluble. Similarly, if the pore generating particles should consist of shredded polystyrene foam, the microfibrillated pulp may initially be suspended in ethyl alcohol or water since the polystyrene foam is insoluble in either of said media. In either case, the ultimate cured product will be washed with a medium in which the polystyrene foam is soluble, such as methylene chloride.

In a variation of the process of the present invention, a pore generating particle may be used, which is heat decomposable, such as ammonium bicarbonate. In this case, the microfibrillated fibers should first be suspended in a medium, such as acetone, in which the ammonium bicarbonate particles are insoluble. The ammonium bicarbonate may then be decomposed in an oven before a suitable cross-linking agent is added in a liquid medium. Of course, after the subsequent curing step, there would be no need to wash the cured cake with any liquid medium since the ammonium bicarbonate would already have been removed therefrom.

If a water soluble pore generating particle is to be utilized in accordance with the present invention, and an aqueous microfibrillated pulp slurry is first made available, then, of course, it will be necessary to exchange the water in the slurry with a liquid medium, such as a non-aqueous solvent, in which the chosen pore generating particle in insoluble.

As pointed out above, a suitable cross-linking agent is added to the microfibrillated slurry either before, during or after the addition of the pore generating particles. After both the pore generating particles and cross-linking agent have been added, the first liquid medium (in which the pore generating particles are insoluble) is evaporated and the resulting solid moist cake is heat cured. After the pore generating particles have been removed either by washing or by heat decomposition, a highly absorbent, retentive, cross-linked cellulose pulp results.

In accordance with the cross-linking procedure, such as that taught in U.S. Pat. No. 3,241,553, cellulosic fibers are subjected to a chemical treatment whereby they are chemically modified to form bonds between the hydroxyl groups in the cellulose molecules. The reactive groups of the cross-linking agent which combines with the hydroxyl groups may exist prior to the reaction with cellulose, as in the case of glyoxal, or they may be generated during the reaction with the cellulose, as in the case of the sodium thiosulfate derivative of divinylsulfone. In order to cross-link cellulose, the cross-linking agent must be at least difunctional with respect to cellulose, e.g., it must react with at least two hydroxyl groups. Formaldehyde, for example, is monofunctional with regard to many substances; it is, however, difunctional with respect to cellulose and is therefore a suitable cross-linking agent. Cellulose may be dry cross-linked or wet cross-linked. However, the procedure utilized in accordance with the present invention is wet cross-linking. A common technique known in the art is to apply the cross-linking agent and a catalyst to the cellulose in an aqueous bath, driving off the water in a drying step, and reacting the cross-linking agent with the cellulose in a subsequent curing step.

Wet cross-linked cellulose is obtained when the cross-linking agent is reacted with the cellulose while the cellulose fibers are not collapsed but are in a swollen state. Ordinarily, the cellulose fibers are maintained in a swollen state by water which is present during the reaction. However, techniques have been developed whereby the cellulose fibers can be maintained in a swollen state in the absence of water by using in lieu thereof an inert, non-volatile substance. Cellulose fibers so treated have the properties of wet cross-linked cellulose even though the reaction takes place in the absense of significant amounts of water.

Suitable agents for the cross-linking of cellulose are formaldehyde, difunctional aldehydes such as glutaraldehyde; dichloro acetic acid, dichloro propanol-2, diepoxides, such as butadiene diepoxides and polyepoxides such as the compound marketed by Shell Chemical Company under the name Eponite 100, N-methylol acrylamide, and divinylsulfone. Most of the above materials require alkaline catalysts, such as sodium hydroxide, to produce wet cross-linked cellulose. However, for the purposes of the present invention, the preferred cross-linking agent is glutaraldehyde, the preferred catalyst utilized in conjunction therewith being zinc chloride. Glutaraldehyde is used in many medical devices (as for instances the device disclosed in U.S. Pat. No. 4,274,410). Zinc chloride was chosen because it not only permits the cross-linking or/polymerization to occur, but it also causes swelling of cellulose which imparts higher resilient characteristics to the final product.

Additional wet cross-linking agents include: condensation products of formaldehyde with organic compounds, such as urea or other chemical compounds which contain at least two active hydrogen groups, particularly dimethylolurea, dimethylol ethyleneurea and imidazolidine derivatives; dicarboxylic acids; dialdehydes such as glyoxal; diisocyanates; divinyl compounds; dihalogen-containing compounds such as dichloroacetone and 1,3-dichloropropanol-2; and halohydrins such as epichlorohydrin etc.

A further suitable cross-linking agent is polyamine/amide epichlorohydrin adduct, a cross-linker manufactured by Hercules under the tradename of Polycup 2002. No catalyst is needed in conjunction with the latter cross-linking agent.

The fibers are in a swollen state at the time of cross-linking in order to obtain wet cross-linked cellulose. Although the swelling is achieved by cross-linking in the presence of water, other swelling agents may be used, such as the preferred zinc chloride referred to above.

Cellulose molecules consist of a large number of glucose units linked to each other through glucoside linkages (oxygen bridges). The preferred catalyst, zinc chloride, reacts with glucoside linkages to form an oxonium salt. This reactive product is more polar and enables the non-reactive cellulose to swell to a greater degree.

One of the preferred cross-linking agents of the present invention, namely glutaraldehyde, undergoes a condensation reaction with cellulose with the loss of water to form an intermolecular cross-link between macromolecular chains. The reaction of cellulose with glutaraldehyde takes place through the formation of hemiacetal and acetal linkages. The addition of glutaraldehyde in the presence of zinc chloride, to the beaten pulp slurry with the subsequent removal of water causes the formation of polyglutaraldehyde and cross-linking of cellulosic fibers. Good results may also be obtained, when 37% W/V of formalin is used in place of glutaraldehyde as the cross-linking agent. The expression "% W/V of formalin" as used herein is intended to designate weight of formalin in grams for every 100 ml of aqueous solution.

The product of the present invention is a sponge-like dried pulp which, either in the sponge-like state or when ground into pulp fluff, exhibits a substantial increase in liquid absorption and retention properties as contrasted with pulp provided by conventional means. The improvement in the absorption properties is probably a result of the unusal morphology resulting from preparing pulp by the teachings herein.

After the product is washed and dried, the dried product is pressed under high pressure to form a thin flat sheet. The resultant pressed product is capable of retaining good absorbency and retention and thus differs substantially from the product of U.S. Pat. No. 4,474,949 which does not include the cross-linking step.

The invention will be further described by reference to the following examples wherein there is disclosed preferred embodiments of the present invention. However, it is to be appreciated that such examples are illustrative but not limitative of the broader aspects of the inventive concept.

The percentages of ingredients in the slurry are given herein as weight of the ingredient in grams for each 100 ml of slurry.

In the following Examples, the particle size range of the pore generating particles was between 0.1 and 1.0 mm equivalent spherical diameter.

EXAMPLE 1

Microfibrillated cellulose is a highly beaten cellulose prepared generally by the process disclosed in U.S. Pat. No. 4,474,949. A satisfactory degree of fibrillation (Freeness below 50 Canadian Standard Freeness) can be obtained on a laboratory Valley Beater after 90 minutes. However, the beating time is varied according to the type of beater used. The same Freeness can be achieved with a Jordan-type beater or a double disc refiner in approximately 30 minutes at a 4% consistency. The beaten pulp slurry is processed as is or dewatered by a Buchner funnel or centrifuge. A preferred method of preparing a 2% slurry is as follows:

The raw material was prepared by soaking a southern pine bleached kraft pulp board with water and beating it on a Valley Beater at a consistency of 2%. The Valley Beater, Model No. 73-13-1-1/2 Niagra, obtained from the Voith Company of Appleton, Wis., consists of an oval, open cast-iron tub, beater bars and bed plate. The stock is moved counterclockwise by rotation of the beater bars (500±10 rpm). The beating action takes place between bars and the bed plate. In order to prepare the raw material, initially, about 430 grams of air-dried pulp board (6.5% moisture) were soaked in 10 liters of water for a minimum of 4 hours. The pulp boards were then cut into small pieces and processed in the Valley Beater with an additional 10 liters of water for 10 minutes (no beating) to prepare a slurry of 2% consistency. The beating process, started by applying a load to the beater bars, was continued for a period of 4 hours. The beaten slurry was then placed in a reaction vessel and heated to 80° C. The reaction vessel is a unit manufactured by Dover Corporation. The unit (Model No. TA-40-SP-1972) is constructed of stainless steel and it is steamed jacketed for heating at maximum water pressure of 25 psi absolute at 300° F. The maximum capacity of this unit is 100 liters.

Mixing was carried out by a wall scraper. It takes 700 grams of centrifugal force for 30 minutes to dewater 5 gallons of 2% microfibrillated cellulose to a 24% consistency cake. The actual dewatering time is dependent on the equipment, amount of vacuum or centrifugal force, solid content and degree of fibrillation. The high consistency cake was then stored in an air tight container for further experiment.

Sodium Sulfate Process

In this process sodium sulfate was used to generate the pores. However, since sodium sulfate will dissolve in water, a large quantity of water should not be present. Therefore, the high consistency microfibrillated cellulose (24% consistency cake) was redispersed in acetone and mixed with an explosion-proof mixer for 5 minutes. Redispersion and washing was repeated 4 times until little or no water was left in the samples. An appropriate amount of acetone was added to obtain a 2% consistency slurry. Based on each gram of the oven-dried weight of fiber, 0.5 grams (50% is water) of glutaraldehyde and 0.8 grams of zinc chloride were first dissolved in the slurry. Then 25 grams of sodium sulfate salt for each gram of fiber were gradually added to the slurry while mixing. The paste-like material was then evenly spread on polypropylene trays and left under the hood for excess acetone to evaporate. The semi-dry cake was placed in a 100° C. oven to cure for 1 hour. The cured cake was washed to remove the salt for 30 minutes, dried and pressed to 5,000 lbs. per square inch and tested by the porous plate method. The press which was utilized is manufactured by Wabash Metal Company. It has a controlled heating system and possesses a 6-inch compression stroke and a maximum compression force of 30 tons. The upper and lower plenums have the capability of heating to 300° C. The densified samples were then cut and stored in plastic bags for evaluation.

EXAMPLE 2

Ammonium Bicarbonate Process

In utilizing ammonium bicarbonate as the pore generating particle, a low water content microfibrillated cellulose is also required. Accordingly, the same procedure was carried out as in Example 1. The low water content microfibrillated cellulose was slurried in acetone and mixed with 25 grams of ammonium bicarbonate for each gm of fiber. Since ammonium bicarbonate is alkaline it would react with zinc chloride which is thus precluded as a catalyst. Moreover, ammonium bicarbonate reacts with glutaraldehyde and produces an objectionable yellow color. Therefore, the ammonium bicarbonate was first decomposed in the oven and then the resultant low density web was cross-linked with the same amount of zinc chloride and glutaraldehyde in an acetone medium as used in Example 1. As in Example 1, after the cross-linking agent is added, the material was then evenly spaced on polypropylene trays and left under the hood for excess acetone to evaporate. Thereafter the semi-dry cake was placed in a 100° C. oven to cure for 1 hour. Since the ammonium bicarbonate had already been removed by decomposition in the oven, there was no need to wash the cured cake. The cake was dried and pressed to 5,000 lbs. per square inch and tested by the porous plate method.

EXAMPLE 3

Non-Aqueous System

For this process, polystyrene foam was utilized to keep the microfibrillated cellulose fibrils separated and to generate pores. Polystyrene foam was shredded in an explosion proof blender with alcohol. The microfibrillated cellulose prepared in accordance with Example 1 was then dewatered by alcohol rather than acetone. The microfibrillated cellulose was reslurried in alcohol and mixed with shredded polystyrene on a one to one basis. The same quantities, by weight, of polystyrene pore generating particles as well as cross-linking agent and catalyst were utilized as in connection with Example 1. The resultant stabilized and cured microfibrillated cellulose cake was washed with methylene chloride to remove the polystyrene. The wet web was then dried in an oven, pressed to 5,000 lbs. per square inch and tested by the porous plate method.

EXAMPLE 4

Aqueous System

This process is similar to that of Example 3 except that polystyrene foam was shredded in water rather than in alcohol and low 2% consistency microfibrillated cellulose was utilized instead of high 24% consistency microfibrillated cellulose. The shredded polystyrene was mixed on a one to one basis with the microfibrillated cellulose. As in the sodium sulfate process of Example 2, based on each gram of the oven-dried weight of the fiber, 0.5 grams (50% is water) of glutaraldehyde and 0.8 grams of zinc chloride were first dissolved in the slurry. (Alternatively, an equivalent amount of polyamine/amide epichlorohydrin adduct, a cross-linker manufactured by Hercules under the tradename of Polycup 2002, could be used in place of the glutaraldehyde, with no catalyst being required). After the cross-linking agent and the polystyrene were added, excess water was vacuum filtered and the mat was cured in an oven. The stabilized mat was then washed with methylene chloride to remove the polystyrene particles. The wet web was then dried in an oven and pressed to 5,000 lbs. per square inch and thereafter tested by the porous plate method. It will be noted that the steps describd are identical to the non-aqueous system polystyrene foam process of Example 3. However, the dewatering step and solvent (alcohol) utilization are eliminated in this procedure.

For the purposes of the following discussion, the products of Examples 1 and 2 are designated as MFCS-IV meaning microfibrillated cellulose sheet-IV. The products of Examples 3 and 4 are designated as MFCS-V. The product of U.S. Pat. No. 4,474,949, prepared by microfibrillation and freeze drying but without cross-linking, is designated as MFCS-I.

The products of Examples 1 through 4 were tested for absorption properties at different densities by the porous plate method (Table 1).

The Porous Plate Testing apparatus, is described in detail in Textile Res. J. 37 pp. 356–366, 1967 and a modified testing procedure has been further described as "Gravimetric Absorbency Testing System" in a monograph on "Absorbency" in Textile Science and Technology, volume 7, page 67, edited by Pronoy K. Chatterjee, published in 1985 by Elsevier Science Publishers BV, P.O. Box 211, 1000 AE Amsterdam, The Netherlands. Briefly, this test involves placing the sample in what is essentially a Buchner Funnel having a porous bottom plate and holding the sample in place by applying thereon a standard weight to maintain a standardized confining pressure. The porous plate is placed in contact with a reservoir of fluid and the sample is allowed to absorb the fluid through the porous plate until saturated. By maintaining the samples at essentially the level of the reservoir, the fluid absorbed is subjected to essentially zero hydraulic head with respect to the reservoir. The weight of fluid absorbed, divided by the weight of the sample, is termed the Maximum Capacity. As the sample absorbs fluid, a measurement of weight absorbed as a function of time is made. The slope of this curve at the time absorption begins is termed the Initial Rate of Absorption. To determine fluid retention, the saturated sample is elevated with respect to the reservoir, thereby imposing a hydraulic head upon the fluid absorbed, the head being arbitrarily chosen as 35.5 cm. of fluid. The apparatus is provided with means for measuring the weight of fluid retained under the hydraulic head. Retention values are reported as the weight retained per unit weight of sample. The results of testing the samples are recorded below in Table 1. The testing fluid in each case is a 1% NaCl aqueous solution, and the confining pressure is 4.8 grams/cm$^2$.

TABLE 1

EVALUATION OF MICROFIBRILLAR CELLULOSE
Method: Porous Plate Test With
1% Aqueous NaCl
Sample Density: 0.4 g/cm$^3$

| Sample | Process | Absorbency Max Cap. (g/g) | Ret'n (g/g) | Z Direction Expansion % |
|---|---|---|---|---|
| Filter Paper | Control No freeze drying No X-link No beating | 3 | 2 | 0 |
| Fluff Pulp | Control No freeze drying No X-link No beating | 5 | 3 | 0 |
| MFCS-I | Freeze-dried (Control, no X-link) | 6 | 5 | 0 |
| Fluff Pulp | Freeze-dried (X-link) No beating | 10 | 3 | 200 |
| MFCS-IV (Na$_2$SO$_4$ or ammonium bicarbonate) Examples 1 and 2 | Salts (X-link) | 15 | 7 | 400 |
| MFCS-V Examples 3 | Polystyrene (X-link) | 15 | 6 | 400 |

TABLE 1-continued

EVALUATION OF MICROFIBRILLAR CELLULOSE
Method: Porous Plate Test With
1% Aqueous NaCl
Sample Density: 0.4 g/cm³

| Sample | Process | Absorbency Max Cap. (g/g) | Ret'n (g/g) | Z Direction Expansion % |
|---|---|---|---|---|
| and 4) | | | | |

The conditions under which the pulp control were produced, were similar to the corresponding conditions for preparing the product of Example 1, except as noted in Table 1.

As can be seen from Table 1, the products of the present invention as set forth in Examples 1 through 4 (namely MFCS-IV and MFCS-V) are compared with freeze dried, non-beaten, cross-linked fluff pulp, ordinary filter paper and fluff pulp (which is non beaten, non freeze dried, non cross-linked) as well as the product of U.S. Pat. No. 4,474,949 (designated MFCS-I) which consists of non cross-linked freeze dried microfibrillated wood pulp cellulose. It will be noted that all of the samples in Table 1 have been compressed to a sample density of 0.4 g/cc. At this sample density, MFCS-IV and MFCS-V achieve high absorbency at said high density, namely 15 cc/g in each case. It is evident from the data in Table 1 that the densified products of present Examples 1 through 4 are significantly superior in absorption than their non cross-linked counterpart MFCS-I disclosed in U.S. Pat. No. 4,474,949. Cross-linking a non-fibrillated fluff pulp also improves the absorption capacity, but not to the extent that could be achieved by the microfibrillated batch. In this connection it will be noted that the maximum capacity of MFCS-IV and MFCS-V at 0.4 g/cm³ density is 15 g/g whereas the maximum capacity at the same density of MFCS-I is only 6 g/g, i.e., 2½ times as great. It is thus very surprising that the process of the present invention provides such an extraordinary improvement over the process of U.S. Pat. No. 4,474,949.

Although MFCS-IV and MFCS-V have a maximum porous plate capacity, as indicated in Table 1 of 15 g/g the presently claimed invention is also intended to encompass those products having a maximum porous plate capacity of at least about 10 g/g with a testing fluid of 1% sodium chloride aqueous solution. Similarly, although it is indicated in Table 1 that MFCS-IV has a porous plate retention of 7 g/g and MFCS-V has a porous plate retention of 6 g/g, nevertheless the present invention is intended to encompass products having a porous plate retention of at least about 5 g/g.

While Table 1 indicates that a significant improvement was obtained with a density level of 0.4 g/cm³, improvements have also been found to be quite evident at a density level of 0.1 g/cm³ or higher.

Normally, a 0.5M solution of cupriethylenediamine is a good solvent for cellulose, but if cross-linking is present the latter solvent will not dissolve the cross-linked product. Following the TAPPI method T-230 for viscosity measurements it may be observed that the MFCS-I would easily dissolve in cupriethylenediamine but the products of the present Examples 1 through 4 (namely MFCS-IV and MFCS-V) would not dissolve therein. This phenomenon would indicate the occurrence of cross-linking in the latter case.

The products of present Examples 1 through 4 may be utilized to increase the total absorption capacity of napkins. Furthermore, the compressability of MFCS-IV and MFCS-V in the dry state and their Z direction swelling in the wet state cause these materials to be especially suitable for tampon applications.

While the invention has been described in terms of producing a highly absorbent cellulose pulp, nothing herein should be construed to suggest that the cellulose fibers cannot be otherwise additionally treated by other means to further enhance absorbency combined with other components to produce a composite material for absorbent purposes. Such modification, as well as others which will occur to one skilled in the art, are all within the scope of the teachings of this invention.

We claim:

1. A highly absorbent retentive microfibrilled cross-linked cellulose pulp, said pulp being capable of retaining good absorbency even afer having been highly compressed to a sample density of at least about 0.1 g/cm³, said pulp being made by the process comprising:
   (a) providing a slurry of cellulose fibers in a first liquid medium, said fibers having been extensively beaten to a degree such that at least the outermost of the secondary walls of said cellulose fibers are essentially completely distintegrated into microfibrillar form; having a Canadian Standard Freeness values of less than 100;
   (b) adding so said slurry dispersible pore generating particles having a particle size range of between 0.1 and 5 mm equivalent spherical diameter which are insoluble in said liquid medium, and subsequently dispersing said pore generating particles;
   (c) adding a cross-linking agent to said cellulose fibers during said process and then cross-linking said cellulose fibers, and drying the resulting product.

2. The product of claim 1, wherein said pore generating particles are non-heat-decomposable, said process comprising adding said pore generating particles and said cross-linking agent to said slurry;
   evaporating said liquid medium and heat curing the resulting solid moist cake; washing said heat cured cake with a solvent for said pore generating particles to disperse and remove said pore generating particles and other impurities; and
   drying the resulting cake, whereby said highly absorbent, retentive cellulose pulp results.

3. The product of claim 1, wherein said pore generating particles are heat-decomposable, said process comprising adding said pore generating particles to said slurry;
   evaporating said liquid medium and heat decomposing said pore generating particles so that the latter are dispersed;
   forming a slurry of the resultant cake in said liquid medium and adding said cross-linking agent thereto;
   again evaporating said liquid medium; and
   heat decomposing said pore generating particles so that the latter are dispersed;
   forming a slurry of the resultant cake in said liquid medium and adding said cross-linking agent thereto; again evaporating said liquid medium; and heat curing and drying the resultant solid moist cake, whereby said highly absorbent, retentive cellulose pulp results.

4. The product of claim 1, which comprises additionally compressing said absorbent element to produce a densified thin sheet having a sample density of at least about 0.1 g/cm³.

5. The product of claim 4, said absorbent element having been densified under pressure to a sample density of at least about 0.4 g/cm³.

6. The product of claim 2 in which microfibrillated pulp is dispersed in acetone, whereafter glutaraldehyde as a cross-linking agent and zinc chloride as a catalyst are added, followed by the addition of pore generating particles comprising sodium sulfate or sodium chloride, the acetone is then evaporated and the resulting solid moist cake is heat cured, whereafter the resulting cake is washed with water to remove the sodium sulfate or sodium chloride and the washed cake is then dried and pressed to produce a densified thin sheet.

7. The product of claim 3 wherein microfibrillated pulp is dispersed in acetone, whereafter pore generating particles consisting of ammonium bicarbonate are added, the ammonium bicarbonate is then heat decomposed after which said cross-linking agent is added to said pulp, in an acetone medium, the acetone is then evaporated and the resulting solid moist cake is heat cured and pressed to produce a densified thin sheet.

8. The product of claim 2, in which said pore generating particles consist of shredded polystyrene which are added directly to an aqueous slurry of microfibrillated fibers; said cross-linking agent consists of a polyamine/amide epichlorohydrin adduct, and said solvent comprises methylene chloride.

9. The product of claim 1, in which water in an aqueous slurry of microfibrillated fibers is first exchanged with ethyl alcohol, pore generating particles consisting of shredded polystyrene are then added, said cross-linking agent consisting of glutaraldehyde together with zinc chloride as a catalyst, and said solvent comprising methylene chloride.

10. An absorbent product comprising as an absorbent element therein, the cellulose pulp according to claim 1.

11. An absorbent product comprising as an absorbent element therein, the cellulose pulp according to claim 2.

12. An absorbent product comprising as an absorbent element therein, the cellulose pulp according to claim 3.

13. The product of claim 10, wherein said product is a sanitary napkin.

14. The product of claim 10, wherein said product is a catamenial tampon.

15. The product of claim 10, wherein said product is a disposable diaper.

16. The product of claim 10, wherein said product is a wound dressing.

17. The product of claim 1, wherein the starting cellulose fibers are wood pulp.

* * * * *

UNITED STATES PATENT AND TRADEMARK OFFICE
CERTIFICATE OF CORRECTION

PATENT NO. : 4,911,700

DATED : March 27, 1990

INVENTOR(S) : Kambiz B. Makoui, et al.

It is certified that error appears in the above-identified patent and that said Letters Patent is hereby corrected as shown below:

Claim 1(b), column 12, line 28, change "adding so" to read "adding to"

Claim 4, column 12, line 67, delete "which" and insert "wherein said process"

Claim 6, column 13, line 6, should read "The product of the process. . ."

Signed and Sealed this

Fifth Day of January, 1993

Attest:

DOUGLAS B. COMER

Attesting Officer

Acting Commissioner of Patents and Trademarks